United States Patent
Bratcher et al.

(10) Patent No.: US 6,497,894 B1
(45) Date of Patent: Dec. 24, 2002

(54) AQUEOUS DISPERSION OF CURED SILICONE RUBBER PARTICLES

(75) Inventors: Tammy Lea Bratcher, Cloverport, KY (US); Kazuo Kobayashi, Chiba (JP); Donald Taylor Liles, Midland, MI (US); Yoshitsugu Morita, Chiba (JP)

(73) Assignees: Dow Corning Corporation, Midland, MI (US); Dow Corning Toray Silicone Co., Ltd., Tokyo (JP)

( * ) Notice: Subject to any disclaimer, the term of this patent is extended or adjusted under 35 U.S.C. 154(b) by 0 days.

(21) Appl. No.: 09/923,148

(22) Filed: Aug. 6, 2001

(51) Int. Cl.$^7$ .................. A01N 25/04; H01N 55/10; C08L 83/04
(52) U.S. Cl. .................. 424/405; 523/122; 524/284; 524/287; 524/323; 524/379; 524/384; 524/386; 524/388
(58) Field of Search .................. 424/405; 523/122; 524/284, 287, 323, 386, 384, 379, 588

(56) References Cited

U.S. PATENT DOCUMENTS

| | | | | |
|---|---|---|---|---|
| 5,708,057 A | * | 1/1998 | Morita et al. ............ | 523/402 |
| 5,871,761 A | * | 2/1999 | Kuwata et al. ............ | 424/401 |
| 5,928,660 A | * | 7/1999 | Kobayashi et al. ......... | 424/401 |
| 6,183,766 B1 | * | 2/2001 | Sine et al. ............... | 424/401 |
| 6,238,656 B1 | * | 5/2001 | Morita et al. ............ | 424/70.12 |
| 6,294,186 B1 | * | 9/2001 | Beerse et al. ............. | 424/401 |
| 6,399,081 B1 | * | 6/2002 | Nakanishi et al. ......... | 424/401 |
| 2002/0002124 A1 | * | 1/2002 | Biedermann et al. ....... | 510/218 |

* cited by examiner

Primary Examiner—Robert Dawson
Assistant Examiner—Jeffrey B. Robertson
(74) Attorney, Agent, or Firm—Jim L. DeCesare

(57) ABSTRACT

An aqueous dispersion of cured silicone rubber particles includes as Components, (A) cured silicone rubber particles with an average particle size of 0.1–500 μm; (B) a surface active agent; (C) a thickening agent; (D) an antiseptic agent (i) consisting of phenoxyethanol, chlorphenesin, methylparaben, and benzoic acid, or an antiseptic agent (ii) consisting of phenoxyethanol, chlorphenesin, and sorbic acid; and (E) water. It has superior antiseptic properties and superior anti-mildew properties without impairing the overall stability of the aqueous dispersion.

5 Claims, No Drawings

AQUEOUS DISPERSION OF CURED SILICONE RUBBER PARTICLES

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention relates to an aqueous dispersion of cured silicone rubber particles, more particularly to an aqueous dispersion of cured silicone rubber particles which is imparted with superior antiseptic properties and anti-mildew properties, without impairing stability of the aqueous dispersion.

BACKGROUND OF THE INVENTION

Aqueous dispersions of cured silicone rubber particles have been used as raw materials for cosmetics and in various coatings. Reference may be had, for example, to U.S. Pat. No. 5,708,057 (Jan. 13, 1998), U.S. Pat. No. 5,871,761 (Feb. 16, 1999), 5,928,660 (Jul. 27, 1999), and U.S. Pat. No. 6,238,656 (May 25, 2001). To improve their stability, it is often necessary to increase the content of surface active agents and add more thickening agents to these aqueous dispersions. This, however, has stimulated the growth of mildew and fungi. There is, therefore, a need to improve their antiseptic properties and anti-mildew properties, while at the same time to maintain the stability of the aqueous dispersion of cured silicone rubber particles.

BRIEF SUMMARY OF THE INVENTION

Thus, it is an object of the invention to provide an aqueous dispersion of cured silicone rubber particles possessing superior antiseptic properties and anti-mildew properties without impairing the stability of the aqueous dispersion.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

The aqueous dispersion of cured silicone rubber particles of the invention contains (A) cured silicone rubber particles with an average particle size of 0.1–500 μm; (B) a surface active agent; (C) a thickening agent; (D) (i) an antiseptic agent consisting of phenoxyethanol, chlorphenesin, methylparaben, and benzoic acid, or (D) (ii) an antiseptic agent consisting of phenoxyethanol, chlorphenesin, and sorbic acid; and (E) water. Details of the aqueous dispersion of cured silicone rubber particles of the invention are explained below.

Cured silicone rubber particles (A) have an average particle size of 0.1–500 μm, preferably 0.1–100 μm, more preferably 0.1–50 μm, and especially preferably 0.5–50 μm. The dispersibility of the cured silicone rubber particles in the aqueous dispersion tends to decrease when the average particle size exceeds the upper limit of the range, while on the other hand, it becomes difficult to prepare cured silicone rubber particles when it is below the lower limit of the range. There are no limitations on the shape of Component (A), and the particles can be spherical, oblate, or irregular, but a spherical shape is preferred due to the ease of manufacture. There are no limitations concerning the consistency of Component (A), and the particles can be rubbery or gel-like. In addition, when the aqueous dispersion of cured silicone rubber particles is compounded with cosmetics and coating materials, the Type A durometer hardness of Component (A) is preferably not more than 80, more preferably not more than 65, as defined in Japanese Industrial Standard (JIS) Test Procedure K-6253.

Spherical or irregular cured silicone rubber particles can be prepared by subjecting alkoxysilanes and other hydrolyzable organosilicon compounds to a reaction involving their hydrolysis and condensation in a basic or an acidic aqueous solution. Cured silicone rubber particles can also be prepared by curing hydrosilation reaction curable silicone compositions, condensation reaction curable silicone compositions, organic peroxide curable silicone compositions, and UV curable silicone compositions, and emulsifying them in water, as illustrated in detail in Reference Example 1 and Application Example 1 herein. It is most preferred, however, to prepare cured silicone rubber particles using an hydrosilation reaction curable composition or a condensation reaction curable silicone composition which is emulsified in water.

Hydrosilation reaction curable silicone compositions are exemplified by compositions containing a polyorganosiloxane having at least two alkenyl groups in its molecule, a polyorganosiloxane having at least two silicon bonded hydrogen atoms in its molecule, and a platinum catalyst. The condensation reaction curable silicone compositions are compositions containing (i) a polyorganosiloxane having hydrolyzable groups such as aminoxy, acetoxy, oxime, alkoxy, or hydroxyl groups, which are bonded to at least two silicon atoms in the molecule, (ii) a silane based crosslinking agent having hydrolyzable groups such as aminoxy, acetoxy, oxime, and alkoxy groups, bonded to at least three silicon atoms in the molecule, and (iii) a condensation reaction catalyst such as an organotin compound or an organotitanium compound.

Component (A) may include an organic, solvent extractable oil inside the cured silicone rubber particles, and which will naturally leak from the particles. Such particles are prepared by a process in which an oil that does not interfere with the curing reaction of a curable silicone composition is compounded into the composition, followed by the emulsification of the composition in water and curing. In another method of making such particles, the oil is added to an aqueous dispersion of the cured silicone rubber particles, and the cured silicone rubber particles become permeated with the oil when agitated. The former process is preferred, however.

These oils can be exemplified by a silicone oil or an organic oil. In the case of the silicone oil, it is a silicone oil that will not interfere with the curing reaction used to form the cured silicone rubber particles. In terms of its molecular structure, it can be a linear silicone oil, a partially branched linear silicone oil, a branched silicone oil, or a cyclic silicone oil, but linear silicone oils are most preferred. Such silicone oils are exemplified by cyclic dimethylsiloxanes, dimethylpolysiloxanes having both terminals of the molecular chain endblocked by trimethylsiloxy groups; dimethylsiloxane methylphenylsiloxane copolymers having both terminals of the molecular chain endblocked by trimethylsiloxy groups; or dimethylsiloxane methyl(3,3,3-trifluoropropyl) siloxane copolymers having both terminals of the molecular chain endblocked by trimethylsiloxy groups.

Some examples of the organic oils are liquid paraffin, isoparaffin, hexyl laurate, isopropyl myristate, myristyl myristate, cetyl myristate, 2-octyldodecyl myristate, isopropyl palmitate, 2-ethylhexyl palmitate, butyl stearate, decyl oleate, 2-octyldodecyl oleate, myristyl lactate, cetyl lactate, lanolin acetate, stearyl alcohol, cetostearyl alcohol, oleyl alcohol, avocado oil, almond oil, olive oil, cacao oil, jojoba oil, sesame oil, safflower oil, soybean oil, Camellia oil, squalane, persic oil, sunflower oil, mink oil, cottonseed oil, coconut oil, egg yolk oil, beef tallow, and pork fat. Some additional examples include glycol ester oils such as polypropylene glycol monooleate and neopentyl glycol-2-ethyl hexanoate; polyhydric alcohol ester oils such as isostearic acid triglyceride and coconut palm oil fatty acid triglyceride; and polyoxyalkylene ether oils such as polyoxyethylene lauryl ether and polyoxypropylene cetyl ether.

While there are no limitations on the viscosity of the silicone or the organic oil, it is preferably a viscosity at 25° C. which is not more than 100,000 mPa·s (centipoise), more preferably not more than 50,000 mPa·s (centipoise), and especially preferably not more than 10,000 mPa·s (centipoise). If its viscosity exceeds the upper limit of the range, it becomes difficult to form cured silicone rubber particles with average particle size of not more than 500 μm. In any case, the oil most preferred is a silicone oil as silicone oils have a superior affinity for cured silicone rubber particles. The content of the oil should not exceed 80 weight percent, preferably not exceed 50 weight percent of the weight of the cured silicone rubber particles. If the upper range is exceeded, it is difficult to prepare cured silicone rubber particles capable of containing the oil.

Component (A) can be present in the aqueous dispersion in amounts of about 25–80 weight percent based on the weight of the aqueous dispersion. The stability of aqueous dispersions in which the content of Component (A) is below the lower limit of the range tends to decrease, and applicability of the dispersions are limited. On the other hand, the handling properties of aqueous dispersions in which the content of Component (A) exceeds the upper limit of the range, tend to deteriorate.

Surface active agent Component (B) is a component used to improve the dispersibility of Component (A) in water. Component (B) can be a nonionic surface active agent, a cationic surface active agent, an anionic surface active agent, an amphoteric surface active agent, or a mixtures of two or more of such surface active agents. Nonionic surface active agents are particularly preferred as Component (B).

The nonionic surface active agents can be lipophilic or hydrophilic agents. Representative lipophilic nonionic surface active agents include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexanoate, and diglycerol sorbitan tetra-2-ethylhexanoate; glycerin fatty acids such as monocottonseed oil fatty acid glycerin, glycerin monoerucate, glycerin sesquioleate, glycerin monostearate, glycerin pyroglutamate α,α'-oleate, glycerin monostearate, and glycerin maleate; propylene glycol fatty acid esters such as propylene glycol monostearate; hardened castor oil derivatives; and glycerin alkyl ethers.

Some representative examples of hydrophilic nonionic surface active agents include POE sorbitan fatty acid esters such as polyoxyethylene (POE) sorbitan monooleate, POE sorbitan monostearate, POE sorbitan monooleate, POE sorbitan tetraoleate, POE sorbitol monolaurate, POE sorbitol monooleate, POE sorbitol pentaoleate, and POE sorbitol monostearate; POE glycerin fatty acid esters such as POE glycerin monostearate, POE glycerin monoisostearate, and POE glycerin triisostearate; POE fatty acid esters such as POE monooleate, POE monostearate, POE distearate, POE monodioleate, and ethylene glycol stearate; POE alkyl ethers such as POE lauryl ether, POE oleyl ether, POE stearyl ether, POE behenyl ether, POE-2-octyldodecyl ether, and POE cholestanol ether; and POE alkylphenyl ethers such as POE octylphenyl ether, POE nonylphenyl ether, and POE dinonylphenyl ether.

Further examples of nonionic surface active agents that can be used include pluronic type agents such as pluronic (polyoxyethylene polyoxypropylene glycol); POE.POP alkyl ethers such as POE polyoxypropylene (POP) cetyl ether, POE.POP-2-decyltetradecyl ether, POE.POP monobutyl ether, POE.POP hydrogenated lanolin, and POE-.POP glycerin ether; tetra-POE.tetra-POP ethylenediamine condensation products such as products sold under the name TETRONIC®; POE castor oil and hardened castor oil derivatives such as POE castor oil, POE hardened castor oil, POE hardened castor oil monoisostearate, POE hardened castor oil triisostearate, POE hardened castor oil monopyroglutamate monoisostearate diester, and POE hardened castor oil maleic acid; POE beeswax and lanolin derivatives such as POE sorbitol beeswax; alkanolamides such as coconut oil fatty acid diethanolamide, lauric acid monoethanolamide, and fatty acid isopropanolamide; POE propylene glycol fatty acid esters; POE alkylamines; POE fatty acid amides; sucrose fatty acid esters; POE nonylphenyl formaldehyde condensation products; alkylethoxy dimethylamine oxides; and trioleyl phosphoric acid.

Organosilicon based compounds can be also used as nonionic surface active agents (B) including silicone based nonionic surface active agents such as dimethylpolysiloxane polyethylene glycol, dimethylpolysiloxane polyethylene, dimethylpolysiloxane polyethylene glycol copolymers, and dimethylpolysiloxane methyl(polyoxyethylene) siloxane copolymers.

In any event, whichever type of nonionic surface active agent (B) is used, polyethylene oxide group containing compounds are preferred. For alkyl ethers of polyethylene oxides in particular, it is preferred to use compounds in which at least 10 weight percent of the alkyl groups in the alkyl ether are $C_{13}$ alkyl groups, or compounds such as polyoxyethylene sorbitan monolauryl ether. The content of Component (B) in the aqueous dispersion of the invention is preferably 0.001–10 weight percent, more preferably 0.01–5 weight percent of the aqueous dispersion. The stability of the aqueous dispersion tends to deteriorate if the content of Component (B) in the aqueous dispersion is lower than the lower limit of the range, and the applicability of the aqueous dispersion tends to be limited if it exceeds the upper limit of the range.

Component (C) is a thickening agent for improving the dispersion stability of Component (A) in the aqueous dispersion by increasing the viscosity of the aqueous dispersion. Component (C) is exemplified by clay minerals and water soluble polymers. Some particular examples of Component (C) thickening agent include natural water soluble high polymers and plant derived high polymers such as gum arabic, traganth gum, galactan, guar gum, carob gum, gum Karaya, carrageenan, pectin, agar agar, Cydonian quince seed, algae colloid in the form of brown algae extract, wheat, glycyrrhizic acid, and starch in the form of rice, corn, or potato tuber; microorganism derived high polymers such as xanthan gum, dextran, succinoglucan, and pullulan; animal based high polymers such as collagen, casein, albumin, and gelatin; semi-synthetic water soluble high polymers including starch based high polymers such as carboxymethyl starch and methylhydroxypropyl starch; cellulose based high polymers such as nitrocellulose, ethylcellulose, hydroxypropyl methylcellulose, hydroxyethyl cellulose, sodium cellulose sulfate, hydroxypropyl cellulose, sodium carboxymethyl cellulose (CMC), crystalline cellulose, and cellulose powder; alginic acid based high polymers such as sodium alginate and alginic acid propylene glycol ester; vinyl series high polymers such as polyvinyl alcohol, polyvinyl methyl ether, polyvinylpyrrolidone, and carboxyvinyl polymers such as products sold under the name CARBOPOL® 941; alkyl modified carboxyvinyl polymers such as products sold under the names CARBOPOL® 1342, PEMULEN® TR-1 or PEMULEN® TR-2; polyoxyethylene based high polymers such as polyethylene glycol 1500, polyethylene glycol 4000, and polyethylene glycol 6000; polyoxyethylene polyoxypropylene copolymeric type high polymers; acrylic high polymers such as sodium polyacrylate, polyethylacrylate, and polyacrylamide; polyethyleneimines; cationic polymers; and synthetic water soluble high polymers.

When the aqueous dispersion is intended to be compounded with cosmetic materials, cellulosic polymers, particularly methylhydroxypropyl cellulose and xanthan gum, are preferred as Component (C), because of their weak coagulation properties with respect to the pigments and powders used in cosmetic materials. The content of Component (C) in aqueous dispersions according to the invention is preferably 10–5,000 parts per million (ppm). This level of Component (C) makes it possible to impart a more suitable viscosity to the aqueous dispersion, and it improves the dispersibility and stability of Component (A) in the aqueous dispersion.

Component (D) is the antiseptic agent used to improve antiseptic and anti-mildew properties of the aqueous dispersion without impairing its stability. Component (D) can be (i) an antiseptic agent consisting of phenoxyethanol, chlorphenesin, methylparaben, and benzoic acid; or Component (D) can be (ii) an antiseptic agent consisting of phenoxyethanol, chlorphenesin, and sorbic acid. It should be noted that phenoxyethanol is often referred to as ethylene glycol monophenyl ether or phenyl Cellosolve; chlorphenesin is 3-(4-chlorophenoxy)-1,2-propane diol; and methylparaben is methyl-p-hydroxy benzoate. The structure of chlorphenesin is shown below.

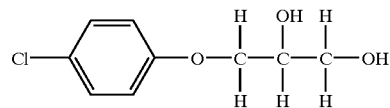

These special combinations of compounds make it possible to impart sufficient antiseptic and anti-mildew properties to the aqueous dispersion containing the cured silicone rubber particles.

Component (D) should contain 40–85 percent by weight of phenoxyethanol and 10–30 percent by weight of chlorphenesin. Water soluble dispersion media such as glycerin and propylene glycol may also be included in Component (D), to improve dispersibility of phenoxyethanol, chlorphenesin, methylparaben, benzoic acid, and sorbic acid, in the aqueous dispersion. Component (D) should be present in the aqueous dispersion in an amount sufficient for the aqueous dispersion to display sufficient antiseptic properties and anti-mildew properties. Typically, it will be present in an amount of 0.1–10 weight percent, preferably 0.5–2.5 weight percent.

Water Component (E) is the medium used to disperse Component (A). While there are no limitations on the content of Component (E) in the aqueous dispersion, it will generally constitute the balance of the aqueous dispersion, depending in each case on the content of the other Components (A)–(D) used to form the aqueous dispersion.

Other than the aqueous dispersion containing Components (A)–(E), there are no limitations concerning the process used in its preparation. Thus, after preparing an aqueous dispersion containing Component (A), Component (B), and Component (E), those components can then be mixed with Components (C) and (D). Alternatively, a curable silicone compositions can be emulsified in an aqueous solution containing Components (B) and (E) and cured, and then the cured silicone composition can be mixed with Components (C) and (D). In any case, heat can be applied when adding Component (D). While thickening agent Component (C) makes it possible to stably disperse Component (A) in water, because the aqueous dispersion contains Component (D), it can still be used as a raw material for cosmetics and coatings, because it possesses antiseptic and anti-mildew properties, even if amounts of Component (B) and Component (C) are increased.

APPLICATION EXAMPLES

The aqueous dispersion of cured silicone rubber particles of the invention is explained in greater detail in the following application examples. The term "viscosity" in the application examples refers to values obtained at 25° C.

Viscosity of Aqueous Dispersion of Cured Silicone Rubber Particles

The viscosity of aqueous dispersions of cured silicone rubber particles was measured using a Bismetron Model VG-DA rotary viscometer of Shibaura Systems Co., Ltd. The device was operated at a rotating speed of 30 rpm, and the values were obtained 3 minutes after the start of rotation.

Average Particle Size of Cured Silicone Rubber Particles

The average particle size of the cured silicone rubber particles was measured using a Model LA-500 laser diffraction type particle size distribution analyzer of Horiba Ltd. The median size, i.e., the particle size corresponding to 50 percent of the cumulative distribution, was used as the average particle size.

Stability at 50° C.

The aqueous dispersion of cured silicone rubber particles was placed in a 100-mL glass vial and kept in an oven at 50° C. for 2 weeks. Compositions in which the emulsified state of the aqueous dispersion remained stable were designated "O", while compositions in which the emulsified state was affected and separation was noticeable, were designated "X".

Freezing Stability 50 gram of an aqueous dispersion of cured silicone rubber particles was placed in a glass bottle loosely stopped with a stopper. Five cycles of testing were carried out, with a single cycle being keeping the bottle at −15° C. for 18 hours followed by keeping it at 25° C. for 6 hours. Again, compositions in which the emulsified state of the aqueous dispersion remained stable were designated "O", while compositions in which the emulsified state was affected and separation was noticeable, were designated "X".

Evaluation of Antiseptic Properties

All formulations were tested in a standard microbiology Laboratory for challenge analysis to determine their ability to resist bacteria, yeast, and mold contamination. Three separate challenge tests were performed.

Initially, a preservative screen was used to narrow the biocide selection options. The preservative screen utilized a mixed inoculum cocktail consisting of Gram negative and Gram positive bacteria and yeast. One ml of this inoculum was added to a 20 ml sample of each formulation every 48 working hours, for a total of six inoculations over a two week period.

After each inoculation, the samples were incubated at 30+/−2° C. for another 48 hours. Following the second incubation period, the samples were evaluated by a traditional pour plate method to determine if the preservative system was able to control and kill the bacteria and yeast. A description of the traditional pour plate method can be found in a text of J. G. Black, *Microbiology Principles and Explorations,* Fourth Edition (Instructors Edition), Pages 141–142; Prentice Hall, (ISBN 0-13-920729-5). The poured plates were read after incubation at 30+/−2° C. for 48 hours.

A second evaluation, the mold capacity challenge test, was performed at the same time as the preservative screen. The mold capacity challenge utilized an inoculum of $10^6$ mold spores. One ml of the inoculation was added to a 9 ml sample of each formulation on the first day of testing. The samples were then incubated for 24 hours at 25+/−2° C. and tested according to a traditional pour plate method to determine if the preservative system was low risk for mold contamination. The poured plates were read after incubation at 25+/−2° C. for 48 hours. The samples were then re-incubated at 25+/−2° C. a total of five weeks for extended evaluation. During this time, they were evaluated weekly, according to the traditional pour plate method, to determine if the formulations were low, medium, or high risk, for mold contamination. If there was no growth after 24 hour incubation they were considered low risk. Low, medium, and high risk assessments were made based on the time it took for the preservative system to kill all microorganisms.

Formulations that passed the preservative screen and the mold capacity challenge testing were then submitted for the bacteria capacity challenge. The bacteria capacity challenge utilized individual inoculums for each of the organisms to be tested. Each sample was split into five separate 99 ml samples to be inoculated with each of five separate one mL inoculums every day for a total of eight working days. Following each inoculation, the formulations were incubated at 30+/−2° C. During a two week period, starting with the first inoculation, the samples were evaluated a total of five times according to a traditional pour plate method, to determine if the formulation was low, medium, or high risk for bacteria and/or yeast contamination. The poured plates were read after incubation at 30+/−2° C. for 48 hours.

Reference Example 1

A water based emulsion of a silicone composition was prepared by using (i) 94.8 parts by weight of a dimethylpolysiloxane with a viscosity of 400 mPa·s having both terminals of its molecular chain endblocked by dimethylvinylsiloxy groups. It contained 2.5 weight percent of a cyclic dimethylsiloxane with a viscosity of about 20 mPa·s. Dimethylpolysiloxane (i) was mixed with (ii) 5.2 parts by weight of a dimethylsiloxane methylhydrogensiloxane copolymer with a viscosity of 50 mPa·s. It had both terminals of its molecular chain blocked by trimethylsiloxy groups in such an amount that the mole ratio of silicon bonded hydrogen atoms in the copolymer (ii) to vinyl groups in dimethylpolysiloxane (i) was 0.95. Dimethylpolysiloxane (i) and copolymer (ii) were emulsified by adding them to 30 parts by weight of an aqueous solution containing five weight percent of a nonionic surfactant which was (iii) a polyoxyethylene (12) alkyl ether. This aqueous solution of nonionic surfactant will be referred to hereinafter as the POE (12) alkyl ether solution. The POE (12) alkyl ether contained 43 weight percent of alkyl groups which were secondary dodecyl groups, while 57 weight percent of the alkyl groups were secondary tridecyl groups. The POE (12) alkyl ether nonionic surfactant solution had an HLB of about 14.5. Emulsification was followed by the addition of another 20.5 parts by weight of demineralized water.

An aqueous dispersion of silicone rubber particles with an average particle size of 3.5 μm was prepared by subjecting the above emulsified silicone composition to hydrosilation. This was carried out by adding to the emulsified silicone composition, a water based emulsion of platinum catalyst with an average particle size of 0.3 μm. The water based emulsion of platinum catalyst was prepared by combining and emulsifying 0.1 parts by weight of a mixed solution of isopropyl alcohol and 1,3-divinyltetramethyldisiloxane, containing a 1,3-divinyltetramethyldisiloxane complex of platinum, and 10.1 parts by weight of POE (12) alkyl ether solution containing one weight percent of POE (12) alkyl ether.

The emulsified silicone composition and the water based emulsion of platinum catalyst were then combined, such that the content of platinum metal in weight units, relative to the emulsified silicone composition, was 4 ppm. The mixture of the two emulsions was allowed to stand for one day. The Type A durometer hardness of the resulting silicone rubber particles was 29, according to the procedure defined in Japanese Industrial Standard (JIS) K-6253. The value obtained according to this procedure was after allowing the mixture to stand at room temperature for one day.

Application Example 1

32.5 parts by weight of POE (12) alkyl ether solution, and 3.2 parts by weight of a similarly constructed nonionic surfactant, POE (3) alkyl ether solution having an HLB of 6.2, were mixed at 80° C., with 18.1 parts by weight of an antiseptic agent. The antiseptic agent contained 8.4 parts by weight of phenoxyethanol, 2.6 parts by weight of chlorphenesin, 3.3 parts by weight of methylparaben, 0.9 parts by weight of benzoic acid, and 2.9 parts by weight of glycerin. An aqueous dispersion of silicone rubber particles (I) was prepared by adding to the mixture, 1530 parts by weight of the aqueous dispersion of silicone rubber particles prepared in Reference Example 1, and then adding 3.4 parts by weight of hydroxypropyl methylcellulose as sold under the name METOLOSE 90SH-15000 by Shin-Etsu Chemical Co., Ltd.

Comparative Example 1

An aqueous dispersion (II) of silicone rubber particles was prepared by repeating Application Example 1 but omitting the antiseptic agent.

Comparative Example 2

An aqueous dispersion (III) of silicone rubber particles was prepared by repeating Application Example 1, except that the antiseptic agent contained 9.7 parts by weight of phenoxyethanol, 2.9 parts by weight of chlorphenesin, 2.2 parts by weight of methylparaben, and 3.3 parts by weight of glycerin. The amounts of the individual components in the antiseptic agent differed from that of Application Example 1, and benzoic acid was not present in the antiseptic agent in this Comparative Example 2.

Reference Example 2

Reference Example 1 was repeated except that the non-ionic surfactant used was 19 parts by weight of an aqueous solution containing 5.3 weight percent of polyoxyethylene sorbitan monolauryl ether, sold under the name REODOL SUPER TW-L120 by Kao Corporation, and referred to hereinafter as REODOL SUPER. Emulsification was followed by the addition of another 30.8 parts by weight of demineralized water. The size of the silicone rubber particles obtained in this Reference Example 2 was 4.1 μm instead of 3.5 μm as in Reference Example 1.

Application Example 2

A mixture was prepared by combining 2.0 parts by weight of xanthan gum, 37.1 parts by weight of REODOL SUPER, and 20.6 parts by weight of an antiseptic agent consisting of 11.1 parts by weight of phenoxyethanol, 3.7 parts by weight of chlorphenesin, 0.9 parts by weight of sorbic acid, and 4.9 parts by weight of propylene glycol. An aqueous dispersion of silicone rubber particles (IV) was prepared by blending 1520 parts by weight of the aqueous dispersion of silicone rubber particles prepared in Reference Example 2 with the mixture.

Comparative Example 3

Application Example 2 was repeated except that the antiseptic agent was omitted in preparing an aqueous dispersion of silicone rubber particles (V).

Comparative Example 4

An aqueous dispersion of silicone rubber particles (VI) was prepared by repeating Application Example 2, except that 15.9 parts by weight of an antiseptic agent was used, and it consisted of 10.5 parts by weight of phenoxyethanol, 0.9 parts by weight of sorbic acid, and 4.5 parts by weight of propylene glycol.

The viscosity, stability at 50° C., and the freezing stability of the aqueous dispersions of silicon rubber particles obtained in the above Application Examples and Comparative Examples are shown in Table 1, their antiseptic properties are shown in Table 2, and their anti-mildew properties are shown in Table 3.

In Table 1, the symbol "O" represents Good Freezing Stability, while symbol X represents Poor Freezing Stability. In Tables 2 and 3, the acronyms NG and TNTC represent No Growth and Too Numerous To Count, respectively.

TABLE 1

|  | Working Example 1 | Working Example 2 | Comparison Example 1 | Comparison Example 2 | Comparison Example 3 | Comparison Example 4 |
| --- | --- | --- | --- | --- | --- | --- |
| Aqueous Dispersion of Silicone Rubber Particles | I | IV | II | III | V | VI |
| Viscosity, mPa · s | 5000 | 4300 | 5400 | 5200 | 4200 | 5000 |
| 50° C. Stability | O | O | O | O | O | O |
| Freezing Stability | O | O | X | O | X | O |

TABLE 2

| Silicone Rubber Particle Water Based Dispersion | Dilution | Cycle 1 | Cycle 2 | Cycle 3 | Cycle 4 | Cycle 5 | Cycle 6 | Pass/Fail |
| --- | --- | --- | --- | --- | --- | --- | --- | --- |
| I | 0.1 | NG | NG | NG | NG | NG | NG | Pass |
| I | 0.01 | NG | NG | NG | NG | NG | NG |  |
| II | 0.1 | NG | NG | NG | NG | NG | NG | Pass |
| II | 0.01 | NG | NG | NG | NG | NG | NG |  |
| III | 0.1 | TNTC | — | — | — | — | — | Fail |
| III | 0.01 | TNTC | — | — | — | — | — |  |
| IV | 0.1 | NG | NG | NG | NG | NG | NG | Pass |
| IV | 0.01 | NG | NG | NG | NG | NG | NG |  |
| V | 0.1 | TNTC | — | — | — | — | — | Fail |
| V | 0.01 | TNTC | — | — | — | — | — |  |
| VI | 0.1 | NG | NG | NG | NG | NG | NG | Pass |
| VI | 0.01 | NG | NG | NG | NG | NG | NG |  |
| Negative |  | NG | NG | NG | NG | NG | NG |  |
| Inoculum, 0.1 ml |  | 122 | 156 | 134 | 112 | 102 | 154 |  |
| Last Positive |  |  |  |  |  |  | TNTC |  |

TABLE 3

| Silicone Rubber Particle Water Based Dispersion | Dilution | Cycle 1 | Cycle 2 | Cycle 3 | Cycle 4 | Cycle 5 | Pass/Fail |
| --- | --- | --- | --- | --- | --- | --- | --- |
| I | 0.1 | TNTC | NG | NG | NG | NG | Pass |
| I | 0.01 | TNTC | NG | NG | NG | NG | (Medium risk) |
| II | 0.1 | TNTC | NG | NG | NG | NG | Pass |
| II | 0.01 | TNTC | NG | NG | NG | NG | (Medium risk) |
| III | 0.1 | TNTC | TNTC | TNTC | TNTC | — | Fail |
| III | 0.01 | TNTC | TNTC | TNTC | TNTC | — | (High risk) |
| IV | 0.1 | TNTC | TNTC | 139 | NG | NG | Fail |
| IV | 0.01 | TNTC | 57 | 18 | NG | NG | (High risk) |
| V | 0.1 | TNTC | TNTC | TNTC | TNTC | — | Fail |
| V | 0.01 | TNTC | TNTC | TNTC | TNTC | — | (High risk) |
| VI | 0.1 | TNTC | TNTC | 67 | 6 | NG | Fail |
| VI | 0.01 | TNTC | 89 | 9 | NG | NG | (High risk) |
| Negative Control | | NG | NG | NG | NG | NG | |
| Positive Control | | TNTC | TNTC | TNTC | TNTC | TNTC | |

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. An aqueous dispersion comprising (A) cured silicone rubber particles with an average particle size of 0.1–500 µm; (B) a surface active agent; (C) a thickening agent; (D) an antiseptic agent (i) consisting of phenoxyethanol, chlorphenesin, methylparaben, and benzoic acid, or an antiseptic agent (ii) consisting of phenoxyethanol, chlorphenesin, and sorbic acid; and (E) water.

2. An aqueous dispersion according to claim 1 wherein Component (B) is a nonionic surface active agent.

3. An aqueous dispersion according to claim 1 wherein Component (C) is a cellulosic based thickening agent.

4. An aqueous dispersion according to claim 1 wherein the aqueous dispersion of cured silicone rubber particles contains 25–80 percent by weight of Component (A); 0.001–10 percent by weight of Component (B); 10–5,000 parts per million of Component (C); 0.1–10 percent by weight of Component (D); the balance of the aqueous dispersion to 100 percent being Component (E).

5. An aqueous dispersion according to claim 4 wherein phenoxyethanol is present in Component (D) (i) and (D) (ii) in amounts of 40–85 weight percent; and chlorphenesin is present in Components (D) (i) and (D) (ii) in amounts of 10–30 weight percent, based on the weight of Component (D) in the aqueous dispersion.

* * * * *